(12) United States Patent
Chen et al.

(10) Patent No.: US 7,088,798 B2
(45) Date of Patent: Aug. 8, 2006

(54) OPERATING METHOD IMPLEMENTED THROUGH A USER INTERFACE FOR A COMPUTED TOMOGRAPHY EXAMINATION

(75) Inventors: Ma Hao Chen, Shanghai (CN); Jian Jun Tang, Shanghai (CN); Yan Xing Yang, Shanghai (CN)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/239,269

(22) Filed: Sep. 29, 2005

(65) Prior Publication Data

US 2006/0072700 A1   Apr. 6, 2006

(30) Foreign Application Priority Data

Sep. 30, 2004   (CN) ........................ 2004 1 0085411

(51) Int. Cl.
*G21K 1/12* (2006.01)
(52) U.S. Cl. ............................. 378/4; 378/16; 378/901
(58) Field of Classification Search ................ 378/901, 378/4, 16, 20
See application file for complete search history.

(56) References Cited

U.S. PATENT DOCUMENTS

| 2003/0016778 A1* | 1/2003 | Tachizaki et al. ............... 378/4 |
| 2005/0008115 A1* | 1/2005 | Tsukagoshi ..................... 378/4 |

* cited by examiner

*Primary Examiner*—David V. Bruce
*Assistant Examiner*—Hoon Song
(74) *Attorney, Agent, or Firm*—Schiff Hardin LLP

(57) ABSTRACT

In an operating method for user interface for a computed tomography examination procedure a menu and a workflow list are merged on a computer screen. One or more scanning programs can be selected in a parameter setting area on the computer screen, each scanning program corresponding to one default patient posture. When an "end of examination" option in the workflow list is selected, job status information is displayed in the parameter setting area, prompting an operator to check the status of the job selected in set reconstruction parameters. Using the interface the user can improve operational efficiency, thereby saving operational time and shortening time spent in examining each patient.

10 Claims, 9 Drawing Sheets

OPERATING METHOD IMPLEMENTED THROUGH A USER INTERFACE FOR A COMPUTED TOMOGRAPHY EXAMINATION

BACKGROUND OF THE INVENTION

1. Field of the Invention

The present invention relates to an operating method implemented through a user interface, and more particularly to such an operating method for a computed tomography examination procedure.

2. Description of the Prior Art

Computed tomography is referred to as CT for short. Different from traditional x-ray imaging, CT employs an x-ray beam to transversely scan a certain region in the human body slice by slice to acquire a certain amount of slice information, which is processed by a computer to obtain a reconstructed image. Such a reconstructed image is referred to as a transverse anatomical image, and can be further processed by the computer to obtain a three-dimensional reconstructed image.

CT, in terms of its external structure, basically embodies a gantry, a patient table and a computer system. The gantry basically includes a high-voltage generator, an x-ray tube, a radiation detector and a data acquisition system. The high voltage generator generates a high voltage for use with the x-ray tube. The x-ray tube and the radiation detector are mounted on opposite sides of tissue to be scanned, facing each other. The x-ray tube generates x-rays and the radiation detector receives the projection information produced by the x-rays transmitted through the human body. Based on the fact that x-ray absorptions of various human tissue (including normal and abnormal tissue) are different, CT divides a certain selected slice in the human body into a number of small cubic blocks of the same volume, referred to as voxels. CT employs an x-ray beam to scan a slice of a certain thickness in a certain region in the human body to obtain projections at different angles, and uses convoluted back projection (also known as filtered back projection) algorithms to reconstruct a tomographic image of the tissue in said region. Each point of the image is represented by a CT value (having a unit of Hu (Hounsfield Unit) corresponding to an attenuation coefficient of different tissue. This point is a basic unit of a CT image and referred to as a pixel. All pixels of an image are arranged in rows and columns, which form an image matrix and thus a CT image.

When an operator uses a CT scanner to examine a patient, a series of operations are to be performed on the CT scanner. Since x-rays from the CT scanner may cause damage to the patient, for safety, the operator should reduce mis-exposure due to various incorrect operations as far as possible. In order to learn how to operate the CT scanner, the operator is generally required to read the user manual of the CT scanner. However, the CT scanner is a complex system, and thus it often takes several weeks or even longer for a novice operator to learn to examine the patient skillfully. Therefore, an intelligent and legible user interface is necessary for the operator to shorten the time he/she spends in learning to operate the CT scanner skillfully, thereby improving operational efficiency and hence shortening time spent in examining each patient.

An examination procedure for the CT scanner typically includes several steps as shown in FIG. 1: registering a patient, positioning the patient on the patient table, selecting a scanning scheme, scanning a scout view, making a tomography scanning plan on the scout view, performing tomography scanning, and ending the scanning.

A display screen for the CT scanner is generally divided into four areas. In FIG. 2, which shows a prior art screen, there is a scout view area at top left, a tomographic image area at top right, a workflow list area at bottom left and a parameter setting area at bottom right. Prior art high-end products (such as Siemens SOMATOM Emotion and Sensation series) allow the operator to select one or more scanning programs (also known as scanning schemes or examination schemes), and thereby to scan multiple regions or scan one region multiple times using different programs. However, CT scanners of this type have the disadvantage that there is no logical sequence relationship between the menu items (such as registration, program, breath prompt and end in FIG. 2) and the options (such as scout view, and scanning one, scanning two, . . . , scanning N in FIG. 2) in the workflow list at bottom left. In other words, the operator, after completing the previous step, will not be quite sure of what to do next due to the fact that the interface fails to provide explicit indication thereof. This will give the operator, especially an inexperienced operator, some difficulty. If the operator unfamiliar with the operating steps operates incorrectly, he or she must make corrections, which is time wasting and thus reduces operational efficiency. Another type of low-end CT scanner (Siemens SOMATOM Smile) of the prior art solves the above-described problem of lack of logical sequence relationship between the menu items and the options by merging the menu items and the options into a list of options, as shown in FIG. 3. However, it is not capable of loading multiple scanning programs, and the operator can choose only one scanning program each time to scan, which lowers operational efficiency.

An operating interface for the CT device that not only enables the operator to operate using only one list of options but also allows scanning of multiple regions in the human body is desirable. Such an operating interface, suitable for scanning multiple regions, is different from the one suitable for scanning only one region as shown in FIG. 3. A substantial modification to the software architecture is needed because a slight change in the interface, sometimes even a change of one option or button, may lead to corresponding alteration of the entire software architecture.

When operating the CT scanner, it is very important to enter a correct patient posture so as to display correct directions (such as up or down, and left or right) on a CT image. In prior art, when the patient posture is to be determined (eight different postures to be selected, depending on head first or feet first, lying supine or lying prone, and left lateral position or right lateral position), the determination is made by clicking at least twice with the mouse at the control console (user interface). However, according to an investigation, for each hospital, if the regions to be examined are identical, the postures of different patients are consistent in most cases whereas inconsistent only in very few cases. Therefore, if each time substantially the same patient posture is to be selected, the number of clicks is unnecessarily increased, lowering operational efficiency. This problem tends to be more severe when there are many patients to be examined.

Besides, during operation, the operator needs to decide whether to perform automatic reconstruction, automatic transfer and automatic filming. Since there are relatively many selected parameters, sometimes the operator may forget whether said automatic reconstruction, automatic transfer and automatic filming have been selected by the end of the operation, and in this event the operator has to return to the previous operating interface to check, which leads to more unnecessary clicks and lowers operational efficiency.

CT scanners known in the art can already meet requirements in terms of examination functions, but must be improved in terms of operational efficiency.

SUMMARY OF THE INVENTION

An object of the present invention is to provide a user interface for a computed tomography examination procedure, which can further increase the operator's operational efficiency over the prior art, thereby saving operational time and shortening the time spent in examining each patient.

This object is achieved according to the present invention by an operating method implemented through a user interface for a computed tomography examination procedure, wherein the user interface as shown on a computer screen and includes a scout view area, a tomographic image area, a workflow list area and a parameter setting area. The method includes the following steps:

(i) a "patient registration" option is displayed in the workflow list on the computer screen, patient parameters being input into the parameter setting area by an operator;

(ii) the workflow list on the computer screen enters a "scanning program selection" option, whereby the operator selects a scanning program from a figure representing the patient body in the parameter setting area and a patient posture from figures of patient posture in the parameter setting area; (iii) a "scout view" option is selected in the workflow list on the computer screen, whereby the operator sets scout view scanning parameters in scanning parameter cards in the parameter setting area, clicks a "load" button to load the scout view scanning parameters, and then presses a "scan" button to perform scout view scanning to form a scout view;

(iv) the scout view is displayed in the scout view area on the computer screen, based on which a scanning plan is determined by the operator, the system then automatically enters the scanning program option selected in step (ii), and then the operator sets tomography scanning parameters in scanning parameter cards in said parameter setting area and tomography reconstruction parameters in reconstruction parameter cards in said parameter setting area, clicks said "load" button to load said tomography scanning parameters, and then presses said "scan" button to perform tomography scanning, a tomographic image being displayed in the tomographic image area on the computer screen;

(v) an "end of examination" option in said workflow list is selected by the operator;

(vi) the examination ends, and the system returns to the operating interface for patient registration, waiting for the operator to input information for the next patient.

The scanning program selected from the figure of the patient body in the parameter setting area by the operator in step (ii) includes one or more scanning programs.

The operator selects multiple scanning programs by clicking an additional bar in said parameter setting area.

After the scanning program is selected, corresponding patient posture is determined automatically in the parameter setting area.

The patient posture includes head first and lying supine, head first and lying prone, head first and lying left lateral, head first and lying right lateral, feet first and lying supine, feet first and lying prone, feet first and lying left lateral, and feet first and lying right lateral.

The "end of examination" option in the workflow list is selected by the operator, job status information being displayed in said parameter setting area.

The job status information includes prompt information for reconstruction, automatic transfer and automatic filming of various scanning programs.

The design approach of the user interface for a computed tomography examination flow according to the present invention has the following advantages:

(a) The user interface for a computed tomography examination flow according to the present invention merges the operating menu and operating options in the workflow list of the prior art, and can execute multiple scanning programs at one time. The operator can operate step by step under the prompt and with the help of the user interface. After a previous step is completed, the operator will be prompted to proceed to the next step by the system without the necessity for selecting the menu and options respectively. The operating steps are clear at a glance, and easy to grasp without referring to a complex specification file. Furthermore, according to the present invention, subsequent operations can be performed after multiple scanning programs are selected, thereby the number of operating steps is decreased, reducing the possibility of incorrect operations and increasing the safety guarantee for patents.

(b) The user interface for a computed tomography examination flow according to the present invention stores default patient postures in various scanning programs. Since patient postures are substantially fixed for CT scanners used in each hospital, at least two clicking operations for examinations of most patients are avoided by adopting the default patient postures; and, even for a few patient postures different from the normal posture, it needs only one more click in the graphical manner than in the case where the default postures are used, thus increasing operational efficiency and saving operational time for each patient.

(c) The user interface for a computed tomography examination flow according to the present invention, before the end of the examination, provides a job status information prompt for the operator to determine whether various selected tasks have been completed successfully or forgotten to be performed, thereby avoiding, in case of the latter, having to repeat the operations at the end of examination, and thus increasing operational efficiency.

DESCRIPTION OF THE PREFERRED EMBODIMENTS

In the following, the present invention will be described in detail in combination with the accompanying figures At first, the scout view area and the tomographic image area on the computer screen are shown blank, and there is only a list of options in the workflow list on the computer screen, no menu being displayed. The "patient registration" option is displayed in the workflow list, and at this moment the "scanning program selection" option displayed in the workflow list on the computer screen is not optional (gray). In accordance with information in the examination list submitted by the patient, the operator inputs patient parameters into the parameter setting area, of which some must be input, such as patient's name, patient ID, sex and birth date.

Figure 1:
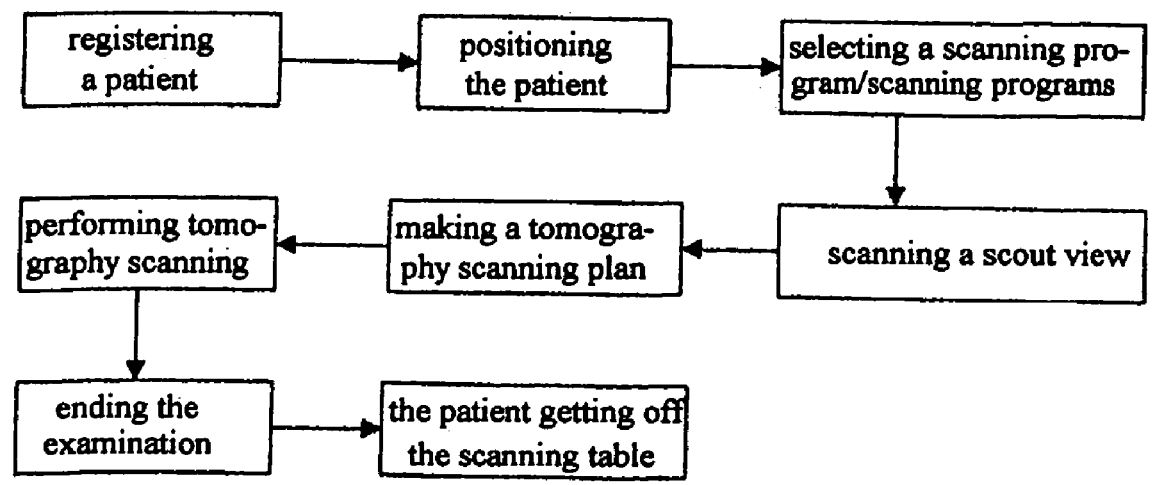
FIG. 1 is a flowchart of operation when the CT scanner is used to perform an examination.
Figure 2:
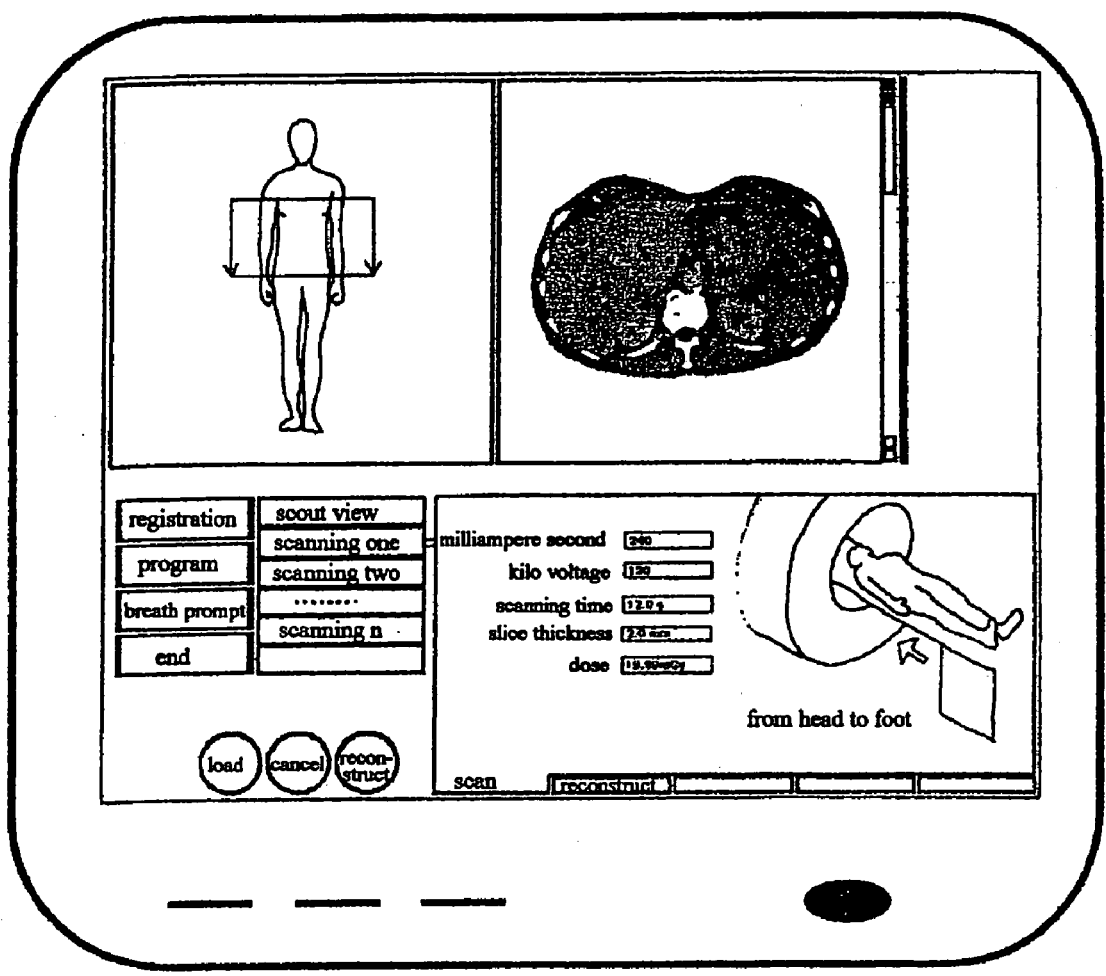
FIG. 2 is the layout of the user interface of high-end products of the prior art displayed on a computer screen, having a scout view area at the top left, a tomographic image area at top right, a workflow list area at the bottom left and a parameter setting area at bottom right.
Figure 3:
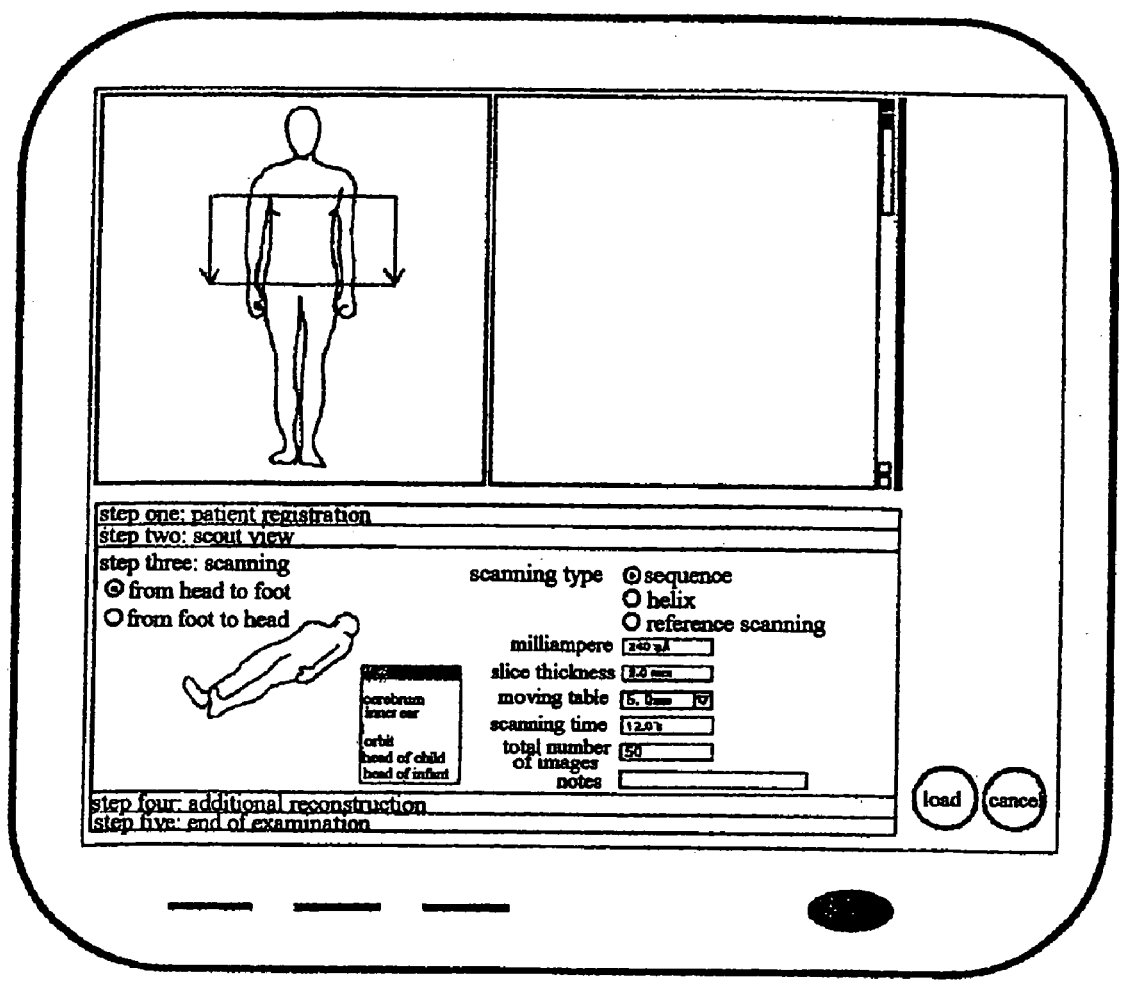
FIG. 3 is the layout of the user interface of low-end products of the prior art displayed on a computer screen, including a scout view area at top left, a tomographic image area at top right, a workflow list area at bottom left and a parameter setting area at bottom right.
Figure 4:
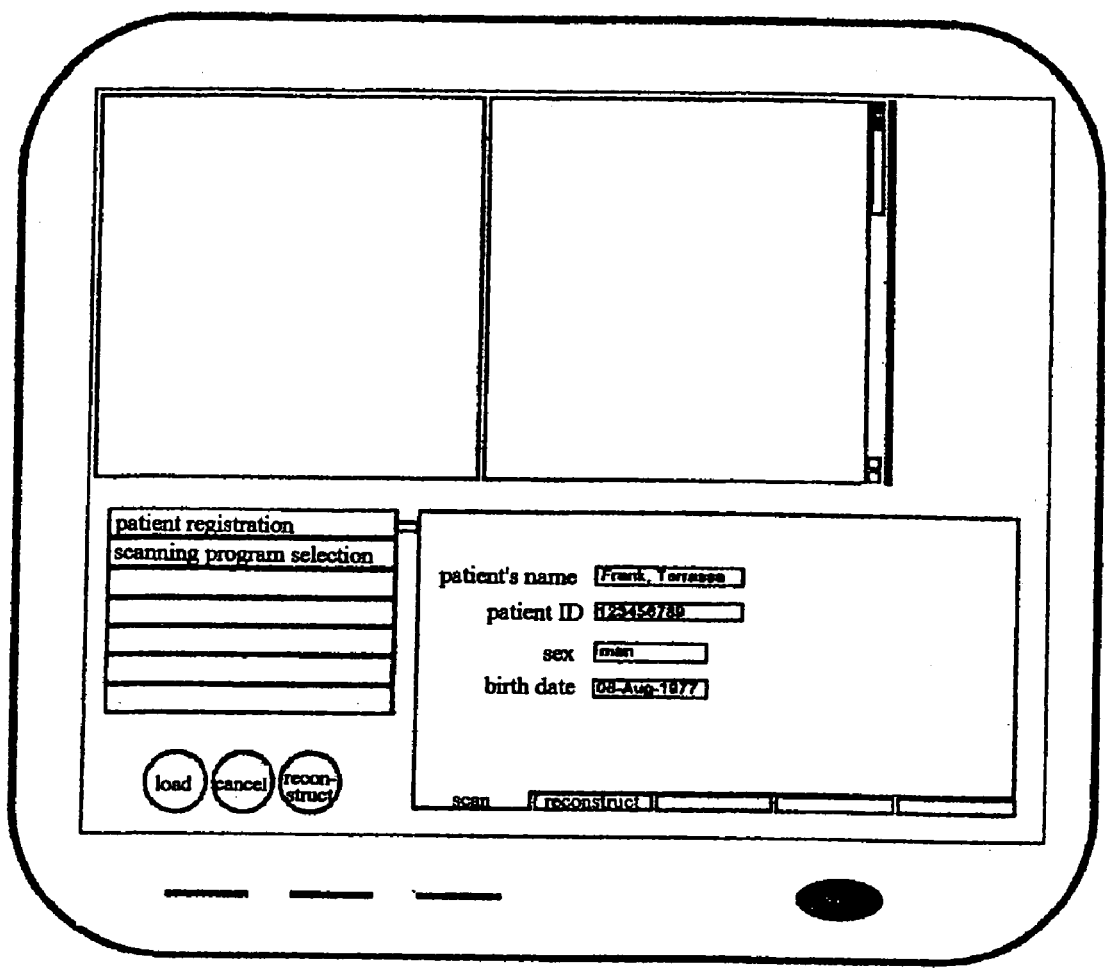
FIG. 4 is patient registration information according to the present invention displayed on a computer screen, the "patient registration" option being displayed in the workflow list on the computer screen and patient parameters to be input in the parameter setting area.
Figure 5:
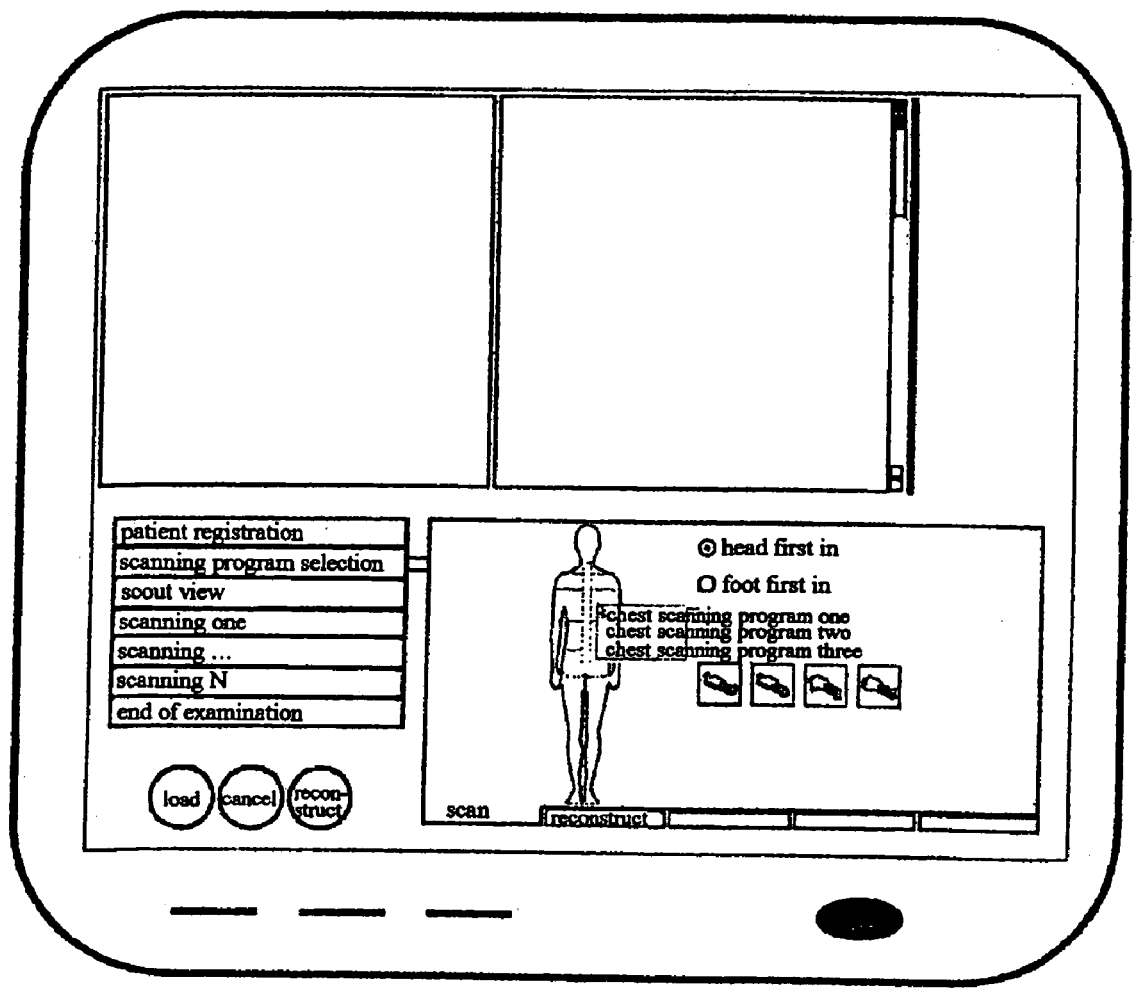
FIG. 5 shows scanning program information according to the present invention displayed on a computer screen, the "scanning program selection" option being displayed in the workflow list on the computer screen and a figure of scanning program region and figures of patient posture to be selected in the parameter setting area.

After the operator inputs said parameters, the "scanning program selection" option turns to an optional state, as shown in FIG. 4. The operator determines a patient posture, i.e., a scanning program, from figures representing patient posture displayed in the parameter setting area, as shown in FIG. 5, the selected region turning red. The operator can select multiple regions to be examined, for example, if the operator wants to select chest and abdomen, the operator can select the chest first, and then select an "additional" item, and then select the abdomen. Hence, both the chest and the abdomen are selected. Different scanning programs for one region, for example, chest scanning program one and chest scanning program two, can be selected in this manner. Different programs for one region or said multiple regions to be examined is regarded as multiple scanning programs. The one or more selected scanning programs appear sequentially under the scout view displayed in the workflow list.

Secondly, the operator determines a patient posture from figures representing patient posture displayed in the parameter setting area, as shown in FIG. 5. The present invention sets default patient postures and stores them in corresponding scanning programs. If the default patient posture is consistent with the actual posture of the patient on the patient table, said default patient posture will be employed, that is to say, there is no need to click; if the default patient posture is inconsistent with the actual posture of the patient on the patient table, the patient posture in the parameter setting area is re-set according to the actual posture of the patient on the patient table, which can be accomplished by clicking once.

Figure 6:
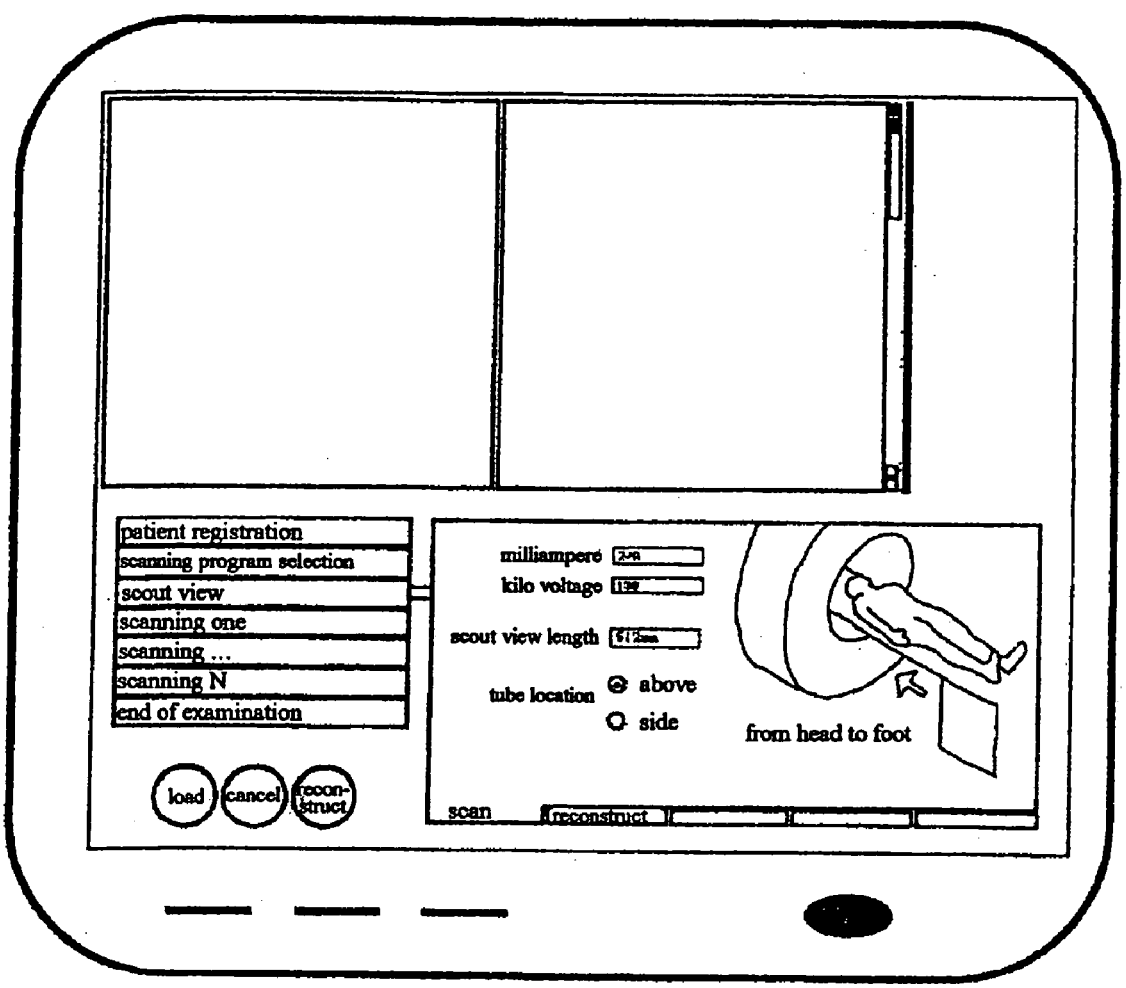
FIG. 6 is scout view information according to the present invention displayed on a computer screen, the "scout view" option being displayed in the workflow list on the computer screen and scout view scanning parameters to be set in the parameter setting area.

After completing the scanning program selection, the operator selects the "scout view" option in the workflow list on the computer screen, as shown in FIG. 6. The operator inputs scout view scanning parameters, such as scout view length, into the scanning parameter setting fields displayed in the parameter setting area, or checks whether settings of the scout view scanning parameters, such as tube location, are correct, and then clicks the "load" button to load the scout view scanning parameters and presses the "scan" button near the keyboard to perform scout view scanning.

Figure 7:
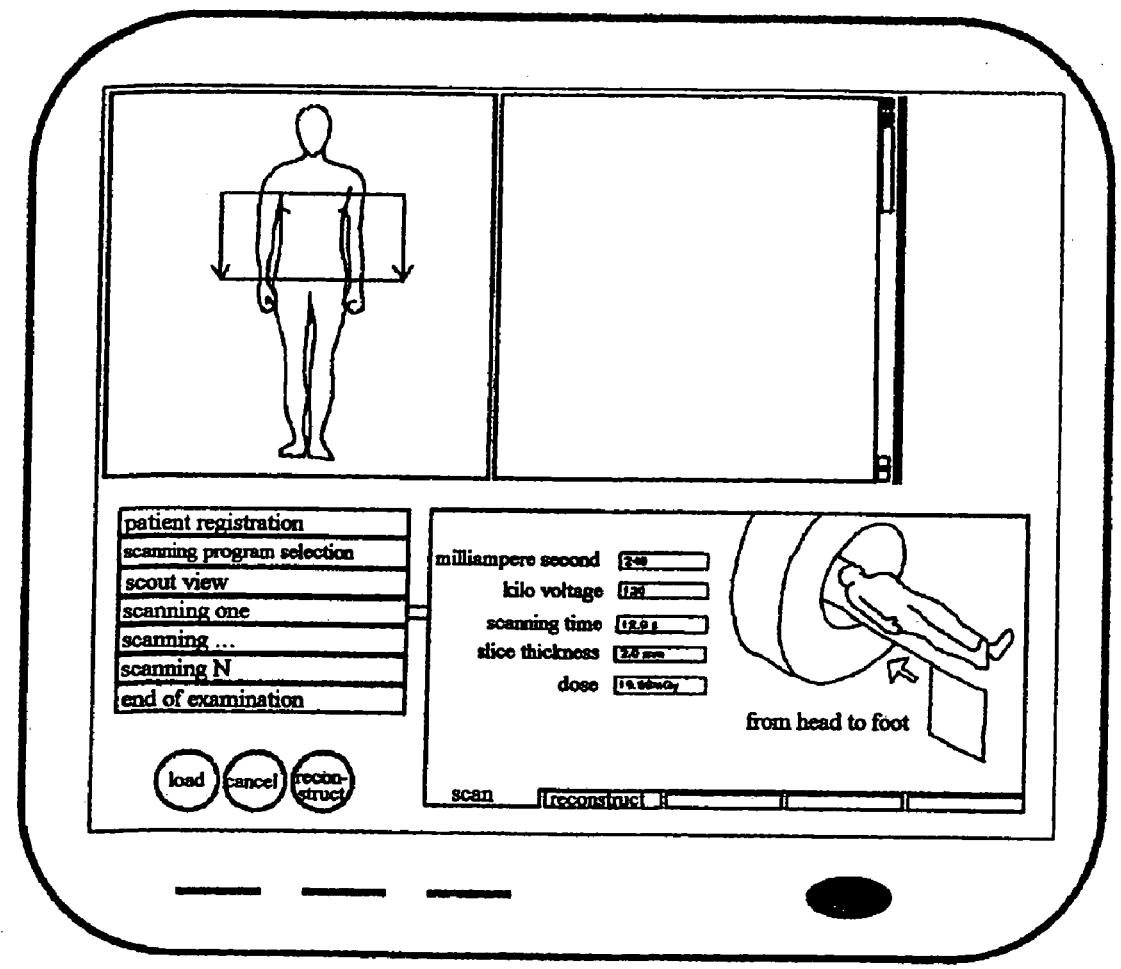
FIG. 7 is specific scanning program information according to the present invention displayed on a computer screen, a scout view being displayed in the scout view area on the computer screen for the operator to determine a scanning plan thereon, selected scanning program options being displayed in the workflow list on the computer screen and scanning parameters to be set in the parameter setting area.

As shown in FIG. 7, the scout view is displayed in the scout view area on the computer screen. The operator determines a scanning plan from the displayed scout view, i.e., selecting an area to be scanned using a frame. At the same time, the system automatically enters the selected tomography scanning program option under the scout view in the workflow list on the computer screen (i.e., the "scanning one" option in case of multiple scanning programs, or the "scanning" option in case of one scanning program). Then the operator sets scanning parameters, such as effective current (milliampere second, mAs), scanning time, slice thickness, dose and so on, in the scanning parameter setting fields displayed in said parameter setting area.

Figure 8:
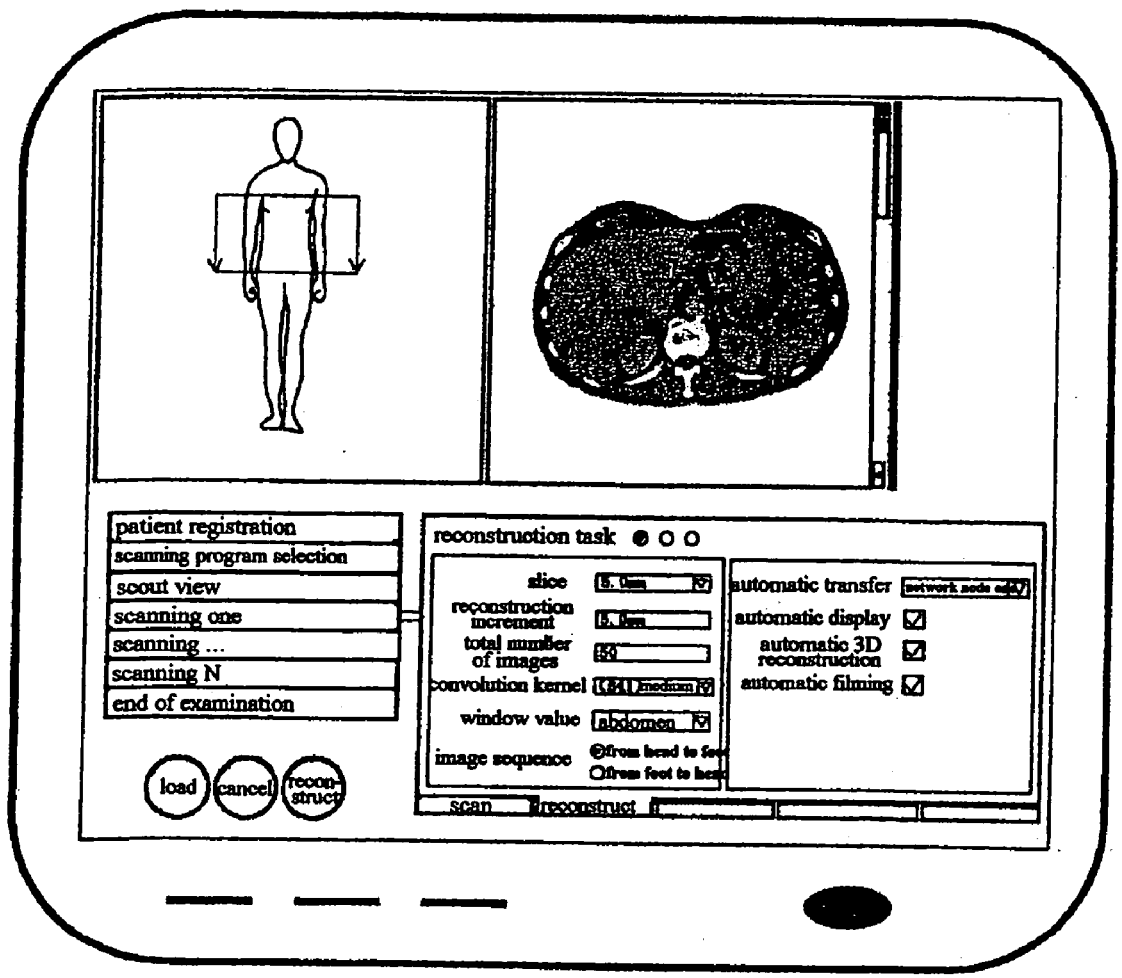
FIG. 8 is specific scanning program information according to the present invention displayed on a computer screen, a scout view being displayed in the scout view area on the computer screen, the selected scanning program options of FIG. 7 in the workflow list on the computer screen, reconstruction parameters to be set in the parameter setting area, and a tomographic image in the tomographic image area on the computer screen.

The operator sets reconstruction parameters, such as slice, reconstruction increment, convolution kernel, window value and so on, in the reconstruction parameter setting fields displayed in said parameter setting area, and then clicks the "load" button to load the tomography scanning parameters to perform tomography scanning. A tomographic image is displayed in the tomographic image area on the computer screen, as shown in FIG. 8.

Figure 9:
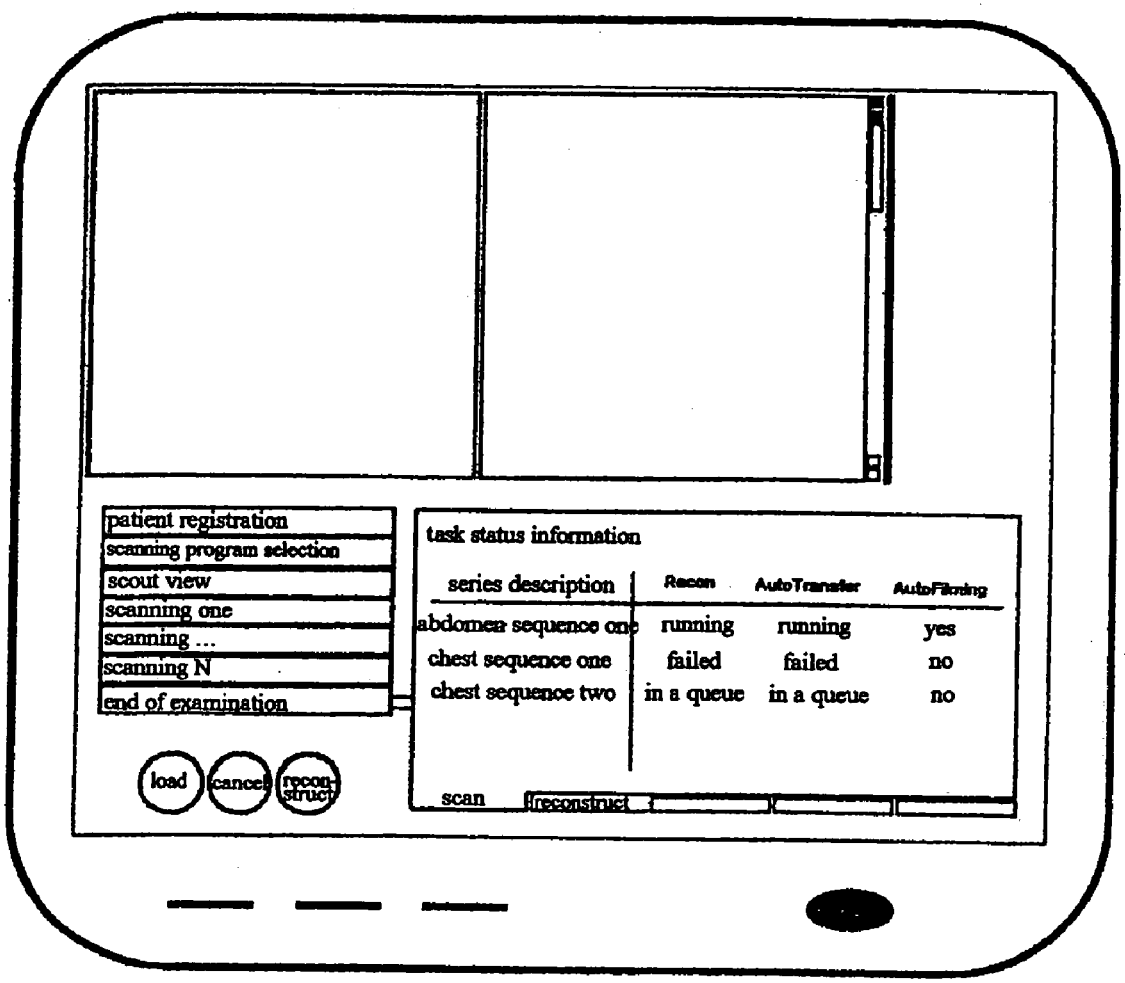
FIG. 9 is job status information displayed on a computer screen, the "end of examination" option being displayed in the workflow list on the computer screen, and status of reconstruction, automatic transfer and automatic filming of the selected scanning programs being displayed in the parameter setting area indicating whether the reconstruction, automatic transfer and automatic filming of the selected scanning programs have been carried out according to the operator's plan.

As shown in FIG. 9, the "end of examination" option in the workflow list is selected, and job status information is displayed in said parameter setting area, which prompts whether the automatic tasks set in the reconstruction parameters by the operator are completed successfully or omitted, for example, whether automatic reconstruction, automatic transfer and automatic filming have been carried out as planned by the operator; if the automatic tasks failed or were omitted the operator returns to the previous step to re-select those automatic tasks that failed or were omitted; otherwise, the operator clicks "enter".

After the end of the examination, the system returns to the operating interface for patient registration, waiting for information for the next patient to be input by the operator.

Although modifications and changes may be suggested by those skilled in the art, it is the intention of the inventor to embody within the patent warranted hereon all changes and modifications as reasonably and properly come within the scope of his contribution to the art.

We claim:

1. A method for conducting a computed tomography examination of a patient implemented through a user interface to a computer of a computed tomography apparatus, said user interface comprising a computerized display screen and at least one input device, said method comprising the steps of:

through said computer, displaying a presentation on said display screen comprising a scout view area, a tomographic image area, a workflow list area, a parameter setting area, and a load button;

automatically highlighting only a patient registration option in said workflow list on said display screen and thereafter only permitting entry of patient parameters into said parameter setting area by an operator via said input device;

upon completion of entry of said patient parameters, automatically highlighting a scanning program selection option in said workflow list and displaying a figure representing a patient body in said parameter setting area and allowing an operator only to select a scanning program by interacting with said figure with said input device, and displaying a plurality of figures respectively representing different patient postures in said parameter setting area and allowing an operator only to select a patient posture by interacting with said plurality of figures representing patient posture with said input device;

after selection of said scanning program and said patient posture, automatically highlighting a scout view option in said workflow list on said display screen and displaying a plurality of scanning parameter cards in said parameter setting area and allowing an operator only to set scout view scanning parameters in said scanning parameter cards and to activate said load button to load said scout view planning parameters into said computer, and said operator then starting said scout view scanning to produce a scout view;

automatically displaying said scout view in said scout view area on said display screen to allow a scanning plan to be determined by an operator, and automatically entering the scanning program selected by the operator and allowing the operator only to set tomography scanning parameters in said scanning parameter cards in said parameter setting area and to set tomography reconstruction parameters in reconstruction parameter cards displayed in said parameter setting area, said operator activating said load button to load said tomography scanning parameters into said computer, and the operator starting said tomography scanning, and automatically displaying a tomographic image in said tomographic image area on said display screen;

upon completion of said tomography scanning, said operator selecting an end of examination option in said workflow list; and automatically ending the examination by restoring blank entries on said display screen in said scout view area, said tomographic image area and said parameter setting area, and re-highlighting said patient registration option in said workflow list.

2. A method as claimed in claim 1 comprising allowing said operator, after automatically highlighting said scanning program selection option in said, workflow list, allowing the operator to select a plurality of scanning programs.

3. A method as claimed in claim 2 comprising after automatically highlighting said scanning program selection option in said workflow list, displaying a bar in said parameter setting area on said display screen and allowing said operator to select said plurality of scanning programs with said input device.

4. A method as claimed in claim 1 comprising after selection of said scanning program, automatically selecting, through said computer, a patient posture in said parameter setting area that is appropriate for the selected scanning program.

5. A method as claimed in claim 1 comprising displaying said plurality of figures respectively representing different patient postures as a plurality of figures representing a patient head first and lying supine, head first and lying prone, head first and lying left lateral, head first and lying right lateral, feet first and lying supine, feet first and lying prone, feet first and lying left lateral and feet first and lying right lateral.

6. A method as claimed in claim 1 comprising upon said end of examination option being selected by the operator, automatically displaying status information in said parameter setting area.

7. A method as claimed in claim 6 comprising including information in said status information comprising prompt information for image reconstruction, automatic data transfer, and automatic filing of said scanning program.

8. A method as claimed in claim 6 comprising using a keyboard as said input device to enter said patient parameters.

9. A method as claimed in claim 1 comprising using a mouse as said input device to allow said operator to interact with said figure representing a patient body, and to select a patient posture by interacting with said plurality of figures representing patient posture.

10. A method as claimed in claim 1 wherein said input device includes a scan button, and comprising pressing said scan button to start each of said scout view scanning and said tomography scanning.

* * * * *